March 16, 1976 S. McGREDY IV Plant Pat. 3,845
ROSE PLANT
Filed Nov. 6, 1974
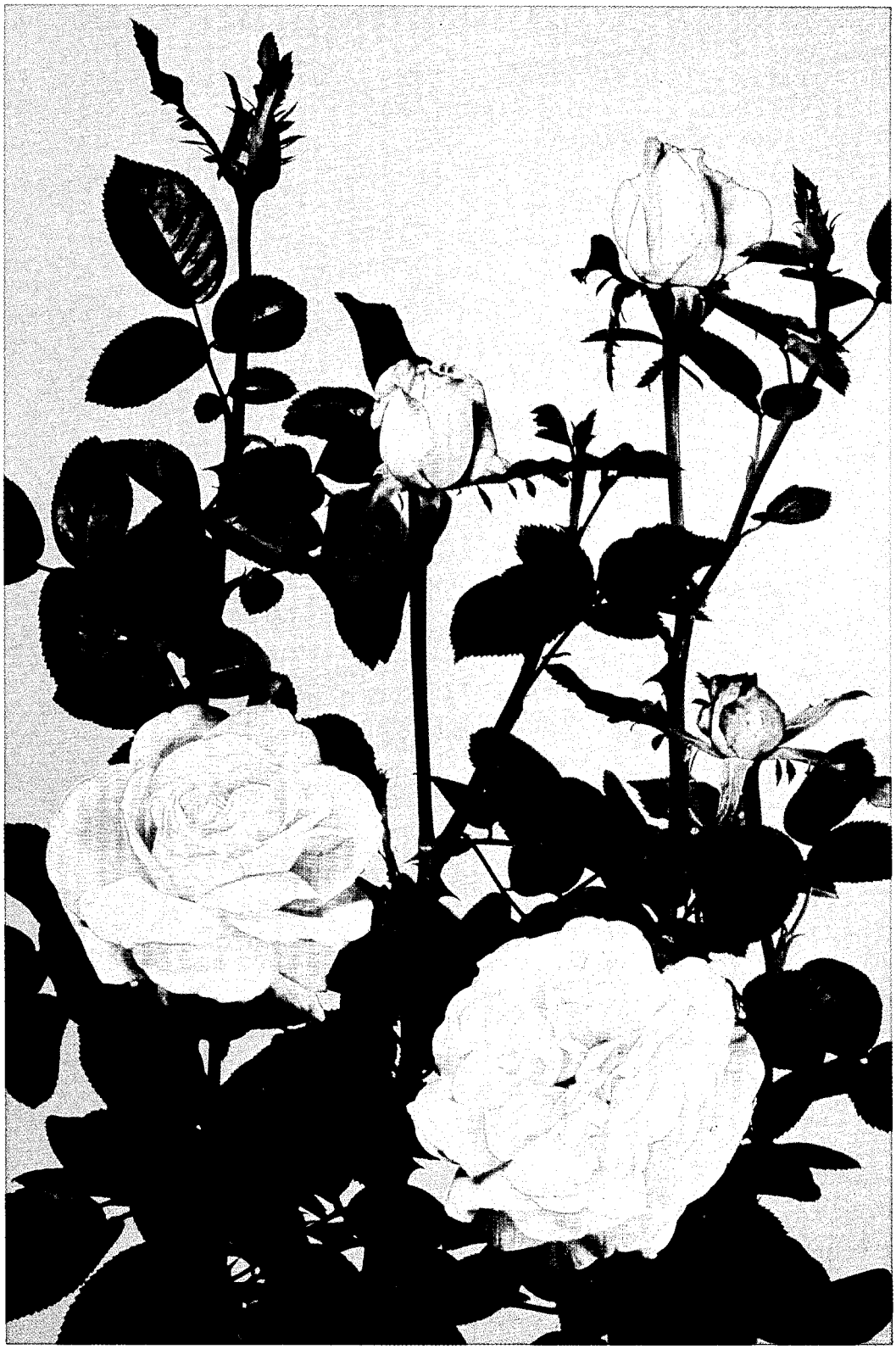

United States Patent

Plant Pat. 3,845

Patented Mar. 16, 1976

3,845

ROSE PLANT

Samuel McGredy IV, Auckland, New Zealand, assignor to Armstrong Nurseries, Inc., Ontario, Calif.

Filed Nov. 6, 1974, Ser. No. 521,366

Int. Cl. A01h 5/00

U.S. Cl. Plt.—11 1 Claim

ABSTRACT OF THE DISCLOSURE

A tall outdoor bush rose plant of the hybrid tea class, having a vigorous much-branched habit of growth and carrying medium length flowering stems rising from upper axillary buds on strong blooming stems. Resistance to mildew is usually better than with plants of the same genus under comparable conditions. The flowers are bi-colored, the upper petal surfaces having an orange-salmon color and the lower petal surfaces being off-white with orange-salmon margins. The general color effect is between deep yellowish pink and vivid red when the flower is freshly opened. This lightens to a shade between deep pink and strong red after the flower has been open for several days. Blooms have a strong citrus-like fragrance.

This invention relates to a new hybrid tea rose. The plant is of the tall bushy outdoor type, cultivated primarily for garden decoration. It was first propagated by Samuel McGredy IV, in Portadown, Northern Ireland, and was propagated in Ontario, Calif., from the budwood of that first propagation. The plant described herein is the plant asexually reproduced in Califorinia, and any comparison to other varieties of hybrid tea rose is based upon plants grown in Ontario, Calif., under comparable conditions.

The seed parent was the variety known as "Arthur Bell," and the pollen parent was "Fragrant Cloud" (Plant Pat. 2,574). The plant holds its distinguishing characteristics through succeeding propagations by budding.

The new variety bears its flowers usually singly on strong medium to long stems, which develop axiallary stems which are of medium length. The fragrance is strong and citrus-like.

The plant differs from its seed parent, Arthur Bell, in that the latter is a yellow flowering floribunda rose, whereas the new cultivar is a hybrid tea rose with orange-salmon and off-white bi-colored blooms. The flowers of Arthur Bell have only about fifteen petals, while the new rose may have fifty to sixty petals, plus petaloids, in each bloom.

The new cultivar may be distinguished from its pollen parent, Fragrant Cloud, for the latter is uniform in coloration, ranging between coral red and geranium red, whereas the new cultivar has bi-colored flowers as just described. The blooms of Fragrant Cloud may have twenty-five to thirty petals, whereas the new cultivar has twice as many petals, plus petaloids.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is average length to long, average to heavy caliper, and more slender at the base than near the receptacle, straight but flexible. It is usually smooth, but sometimes has from few to several stipitate glands. The color is between Light Olive, 10Y5/5, and Moderate Yellow Green, 2.5GY5/5, sometimes overlaid lightly to moderately with colors between Deep Purplish Red 7.5RP3/9, and Dark Red, 5R3/7.

Before the calyx breaks, the bud is small to medium in size, of medium length, and pointed, with foliaceous appendages on the surface of the bud and foliaceous parts extending beyond the tip of the bud equal to three-quarters or more of its length.

As the calyx breaks, the basic color is near Brilliant Greenish Yellow, 10Y9/9, with some shadings near Dark Red, 2.5R3/7, and other shadings near Moderate Yellow Green, 7.5GY5/7.

The inner surface of the sepals is lined sparsely with a fine tomentum. There are a few stipitate glands on the outer surface of the sepals. The sepals are often elongated, developing loosely around the bud (rather than adhering tightly together or to the guard petals).

As the first petal opens, the bud is average in size, of medium length, and urn-shaped. The color on the outside of the petal is near Brilliant Yellow Green, 2.5GY9/8, at the base, and the mid-portion is off-white with margins between Strong Red, 5R4/12, and Dark Red, 5R3/7. The inside surface of the petal is more brilliant than a color between Vivid Red, 5R5/13, and Strong Red, 2.5R5/12, while the basal area is the same color as on the outside of the petal, namely near Brilliant Yellow Green, 2.5GY9/8. The bud opens up well, and is not prevented from opening by cold, hot, wet, or dry weather.

BLOOM

The size of the bloom when fully open is average for roses of the hybrid tea class, being from four to four and one-half inches. The petalage is double, with from fifty to sixty petals, plus fifteen to twenty petaloids arranged irregularly. The bloom is full and high centered.

The petal arrangement may be somewhat irregular, and the petals may be reflexed outward along the lateral margins and/or along the apical margin, or recurved outward. Petals are of medium thickness, with inside slightly outward, or cupped, with or without tips reflexed slightly shiny to satiny, the outside satiny.

The outside petals are very broadly obovate, with apex slightly flattened. Intermediate petals are broadly obovate and slightly mucronate, while the inside petals are obovate to irregular, the apex generally with one shallow notch or irregular. The colors may be modified by being blotched, shaded and/or washed with other colors.

The paragraphs immediately following described color values oberved in a flower newly opened in the month of August. The plant had been grown outdoors, in Ontario, Calif.

The outer surface of the outside petal is near Brilliant Yellow Green, 2.5GY9/8, at the base, blending to off-white in the mid-portion of the petal and then further blending to a color between Strong Red, 5R4/12, and Dark Red, 5R3/7, along the margins. The inner surface of the outside petal is between Deep Yellowish Pink, 5R6/11, and Vivid Red, 5R5/13.

The outer surface of the intermediate petal is near Moderate Yellowish Pink, 7.5R8/6, at the mid-portion, blending with a color near Strong Red, 5R4/12, along the margins. The inner surface of the intermediate petal is between Deep Yellowish Pink, 5R6/11, and Vivid Red, 5R5/13, as on the outside petal.

The inside petal had the same coloration as the intermediate petal, as to both its outer and its inner surfaces.

The paragraphs immediately following describe the color values observed in a bloom which had been open for three days, outdoors, in Ontario, Calif.

The outer surface of the outside petal was off-white in the mid-portion of the petal, blending outwardly to a color between Moderate Red, 2.5R4/10, and Dark Red, 2.5R3/7.

The inner surface of the outside petal was between Deep Pink, 2.5R6/11, and Strong Red, 2.5R5/12.

The outer surface of the inside petal showed a coloration similar to that of the outer surface of the intermediate petal of a newly opened flower, i.e. a mid-portion near Moderate Yellowish Pink, 7.5R8/6, blending along the margins with a color near Strong Red, 5R4/12. The inner surface of the inside petal was near Deep Pink, 2.5R6/11.

The general color effect of the newly opened flower is between Deep Yellowish Pink, 5R6/11, and Vivid Red, 5R5/13. The bloom after being three days open gives a general color effect which is between Deep Pink, 2.5R6/11, and Strong Red, 2.5R5/12. The petals drop off cleanly except for some petaloids, and are not particularly affected by cold, hot, wet or dry weather.

The flower on the bush in the garden persists for from four to five days in the month of August, in the locality named. Cut roses grown outdoors and kept at living room temperatures will last from three to four days in the month of August.

REPRODUCTIVE ORGANS

Stamens: The stamens are average in number, regularly arranged about the pistils, a few of them being mixed with petaloids.

Filaments: The filaments are medium length, being 3 to 7 mm. in length (average 5 mm.), and near Vivid Red, 5R5/13, in color. Most are with anthers.

Anthers: The anthers are of medium size, all opening approximately at once. On both the upper and lower sides, the margins are near Moderate Orange Yellow, 7.5YR8/8, and the remaining portions on both sides are near Pale Orange Yellow, 7.5YR9/4.

Pollen: Pollen is somewhat sparse to moderate, being near Moderate Orange Yellow, 7.5YR8/8, in color.

Pistils: The pistils are from average to many in number, there being approximately 120 of them.

Styles: Styles are uneven, average to long in length, average to heavy in caliper, and separated. They are approximately 10 mm. in length, and rather hairy.

Stigma: The stigma is near Pale Orange Yellow, 7.5YR9/4, in color.

Ovaries: The ovaries are enclosed in and protruding from the calyx.

Hips: This plant does not readily set hips at Ontario, Calif.: only four hips were found on twenty plants. These were short and flat, the width being generally one and one-third times the length. Immature hips were between Strong Yellow Green, 2.5GY7/10, and Strong Yellow Green, 2.5GY6/8, in color. They were smooth, with fleshy walls.

Sepals: The sepals are usually permanent, medium length, and recurved. The color inside was between Strong Yellow Green, 2.5GY7/10, and Strong Yellow Green, 5GY6/8, overlaid with a fine white tomentum—or dead and brown. The outside coloration was the same, i.e. either between Strong Yellow Green, 2.5GY7/10, and Strong Yellow Green, 5GY6/8, or dead and brown.

Seeds: The seeds were few to average in number (3 to 11), and usually small in size.

FOLIAGE

The compound leaves usually comprise three to five leaflets. These are abundant, medium in size, and moderately heavy and glossy. The leaflets are broadly ovate with apex acute, and margin double serrate.

The mature foliage, on its upper surface, is between Moderate Olive Green, 5GY4/3, and Moderate Olive Green, 7.5GY4/4, in color. The undersurface is a medium grayish olive green.

The young foliage, on its upper surface, gives a general color effect of near Moderate Reddish Brown, 10R3/4, and on the undersurface, near Dark Red, 2.5R3/7.

The rachis is average in size, grooved on the upper side, with some stipitate glands on the edges. The underside is sparsely prickly and with a few stipitate glands.

The stipules are medium length, medium width to wide, with medium length points turning out at an angle of less than 90°, recurved slightly toward the stem.

The plant displays a more than average resistance to mildew, when compared with other varieties now in commerce and grown under comparable conditions at Ontario, Calif.

GROWTH

The plant displays a very vigorous growth, is bushy, upright, and much branched in habit, with several relatively long flowering stems arising from upper axillary buds on strong blooming stems. The canes are medium to heavy in caliper.

The main stems are between Light Olive, 7.5Y5/5, and Moderate Yellow Green, 2.5GY5/5, in color. They bear several medium length to long large prickles, which are hooked slightly downward with medium length moderately narrow base. There are several small prickles, and both the large and small prickles are Strong Brown, 5YR4/5, to gray in color. There are no hairs.

The branches are near Moderate Yellow Green, 2.5GY5/5, in color, and bear several large prickles which are medium length to long, hooked slightly downward, with moderately long moderately narrow base. There are from few to several small prickles, and both the large and small prickles are between Strong Yellow Green, 5GY6/8, and Dark Greenish Yellow, 10GY6/7, in color. There are no hairs.

New shoots are near Strong Yellow Green, 5GY6/8, in color, lightly to heavily overlaid with near Deep Purplish Red, 10RP3/10. There are from few to several large prickles, which are medium length, and hooked slightly downward with long narrow base. There are a few small prickles, and both the large and small prickles are between Strong Yellow Green, 5GY6/8, and Deep Purplish Red, 10RP3/10, in color. There are no hairs.

I claim:

1. The new and distinct variety of hybrid tea rose plant substantially as herein illustrated and described, which is characterized by a plurality of the following features, in combination, namely a vigorous upright many-branched habit of growth, with glossy medium-sized foliage, having somewhat better resistance to mildew than plants of the same genus grown under comparable conditions; a nearly continuous blooming habit throughout the season; blooms which have a bi-colored effect of orange-salmon on the upper petal surfaces, and off-white lower surfaces, margined with orange-salmon; a strong citrus-like fragrance; each flowering stem usually carrying a single flower, yet developing relatively medium length blooming stems from upper axillary buds; the flower size ranging from four to four and one-half inches.

No references cited.

ROBERT E. BAGWILL, Primary Examiner

UNITED STATES PATENT AND TRADEMARK OFFICE

CERTIFICATE OF CORRECTION

PATENT NO. : Plant Pat. 3845

DATED : March 16, 1976

INVENTOR(S) : Samuel McGredy IV

It is certified that error appears in the above-identified patent and that said Letters Patent are hereby corrected as shown below:

Column 1, line 40 - "axiallary" should be --axillary--

Column 2, line 47 - "described" should be --describe--

Column 2 - Transpose the entire line 38 with the entire line 39.

Signed and Sealed this

*twenty-second* Day of *June 1976*

[SEAL]

*Attest:*

RUTH C. MASON
*Attesting Officer*

C. MARSHALL DANN
*Commissioner of Patents and Trademarks*